US012778233B2

(12) United States Patent
Hakimi et al.

(10) Patent No.: US 12,778,233 B2
(45) Date of Patent: Nov. 3, 2026

(54) EARMUFF MOUNTING DEVICE

(71) Applicant: JSP Limited, Oxford (GB)

(72) Inventors: Artin Hakimi, Oxford (GB); Clive Johnstone, Oxford (GB)

(73) Assignee: JSP Limited, Oxford (GB)

( * ) Notice: Subject to any disclaimer, the term of this patent is extended or adjusted under 35 U.S.C. 154(b) by 0 days.

(21) Appl. No.: 19/142,580

(22) PCT Filed: Nov. 29, 2023

(86) PCT No.: PCT/GB2023/053086
§ 371 (c)(1),
(2) Date: Jun. 23, 2025

(87) PCT Pub. No.: WO2024/134135
PCT Pub. Date: Jun. 27, 2024

(65) Prior Publication Data

US 2026/0114537 A1 Apr. 30, 2026

(30) Foreign Application Priority Data

Dec. 22, 2022 (GB) ..................................... 2219529

(51) Int. Cl.
*A42B 3/16* (2006.01)
*A61F 11/14* (2006.01)

(52) U.S. Cl.
CPC ................ *A42B 3/16* (2013.01); *A61F 11/14* (2013.01)

(58) Field of Classification Search
CPC ............ A42B 3/16; A42B 3/166; A61F 11/14
See application file for complete search history.

(56) References Cited

U.S. PATENT DOCUMENTS

| | | | | |
|---|---|---|---|---|
| 4,287,614 | A | 9/1981 | Lonnstedt | |
| 5,546,610 | A | 8/1996 | Herzig | |
| 2007/0226865 | A1 | 10/2007 | Lindgren | |
| 2009/0260135 | A1 | 10/2009 | Haselmayer | |
| 2020/0170329 | A1 * | 6/2020 | Bohn | A42B 3/221 |
| 2021/0267299 | A1 | 9/2021 | Ginguenaud | |
| 2025/0234123 | A1 * | 7/2025 | Teetzel | H04R 1/105 |

* cited by examiner

*Primary Examiner* — Katherine M Moran
(74) *Attorney, Agent, or Firm* — Dickinson Wright PLLC; Andrew D. Dorisio

(57) ABSTRACT

A mounting for an earmuff (12) on headwear such as a safety helmet. The mounting includes an adapter (14) for connection to the headwear on its periphery positioned above a wearer's ear. A housing (16) is rotatably mounted on the adapter. A socket (18) has an inner end (46) mounted in the housing and an outer end (44) that projects from the housing. The socket is pivotable about an axis in the plane of rotation of the housing and is biased into a first position in which it extends in a direction perpendicular to the axis of rotation or a second position in which it extends at an angle between the axis of rotation and the direction perpendicular to the axis. The mounting further includes a mounting frame (20) comprising a shaft (58) for engagement in an open end of the socket, and a pair of elongate arms (60, 62) extending from the shaft. Each arm has an extension with a mounting formation (80., 82) for engaging a mounting formation (22) on the shell. Each extension is axially adjustable on its arm, such that when an earmuff is positioned between the arms, the mounting formations on sides of the shell can engage the mounting formations on extensions.

12 Claims, 5 Drawing Sheets

EARMUFF MOUNTING DEVICE

FIELD

This invention relates to a device for mounting an earmuff on an article of headwear, such as a safety helmet. The invention also relates to an earmuff for mounting on an article of headwear, and to an article of headwear with earmuffs.

BACKGROUND

It is common for people working in hazardous environments to require both protecting headwear, such as safety helmets, to protect from impact injury, and ear defenders such as earmuffs for protection against hearing damage due to loud noise. Safety helmets with earmuffs are known for use uses. One problem is that it is sometime necessary to remove the earmuffs from a wearer's ears temporarily or for longer periods when they are not needed and would be inhibiting if left in place over a wearer's ears.

There have been a number of proposals for mounting earmuffs on a pivoting mounting so that the earmuffs can be swung up to rest against the helmet when not needed.

There remains a problem that the position of the earmuff on a wearer's head needs to be correct and so needs to be adjustable. This invention aims to address this problem.

SUMMARY

A first aspect of the invention comprises a device for mounting an earmuff on an article of headwear, wherein the earmuff comprises a shell for positioning over a wearer's ear, with external mounting formations on opposite sides of the shell, the mounting device comprising:

- an adapter for connection to the article of headwear at a location on the periphery of the article of headwear that, in use, is positioned above a wearer's ear;
- a housing rotatably mounted on the adapter;
- a socket having an inner end mounted in the housing and an open outer end projecting from the housing, wherein the socket is pivotable about an axis in the plane of rotation of the housing and is biased into either a first position in which the socket extends in a direction perpendicular to the axis of rotation of the housing or a second position in which the socket extends at an angle between the axis of rotation of the housing and the direction perpendicular to the axis of rotation; and
- a mounting frame comprising a shaft for engagement in the open end of the socket, and a pair of elongate arms extending from the shaft, wherein each arm has an extension with a mounting formation that is engageable with an external mounting formation on the shell, and wherein each extension is axially adjustable on its respective arm, such that when an earmuff is positioned between the arms, the mounting formations on opposite sides of the shell can engage in the mounting formations on respective extensions.

The mounting formations on opposite sides of the shell can be rotatable with respect to the mounting formations on the extensions. In this way, the angle of the earmuff against a wearer's head can be adjusted.

Each extension and its respective arm can have inter-engaging formations that limit axial adjustment to one of a predetermined number of axial positions. For example, the inter-engaging formations can comprise a peg in the arm which engages in a ridged slot in the extension, or vice versa.

The end of the shaft can comprise a latch which engages a lip in the socket to resist removal of the shaft from the socket.

The socket can comprise a pair of lateral extensions at its inner end that engage in a shaped seat in the housing to limit pivoting movement of the socket between the first and second positions. A spring can be located within the housing that acts on the inner end of the socket to hold the lateral extensions in the shaped seat.

The housing can comprise a base and a cover, wherein the inner end of the socket is retained between the based and the cover.

The adapter can comprise a tongue portion that is configured to engage in a corresponding slot in the article of headwear. This can secure the adapter in the desired position on the article of headgear.

The adapter can also comprise a slot for mounting a holder for securing further items to the article of headwear. Such items can be a writing implement and/or a torch which can be removably attached to the holder.

A second aspect of the invention provides an earmuff assembly for mounting on an article of headwear, comprising the device and an earmuff comprising a shell for positioning over a wearer's ear, with external mounting formations on opposite sides of the shell, wherein the earmuff is positioned between the arms and the mounting formations on opposite sides of the shell are engaged in the mounting formations on respective extensions.

A third aspect of the invention provides an article of headwear, comprising a head cover portion adapted to be worn on a wearer's head in use, and the earmuff assembly connected to the article of headwear at a location on the periphery of the head cover portion that, in use, is positioned above a wearer's ear.

Further aspects of the invention are described below in relation to the drawings.

DETAILED DESCRIPTION

Figure 1:
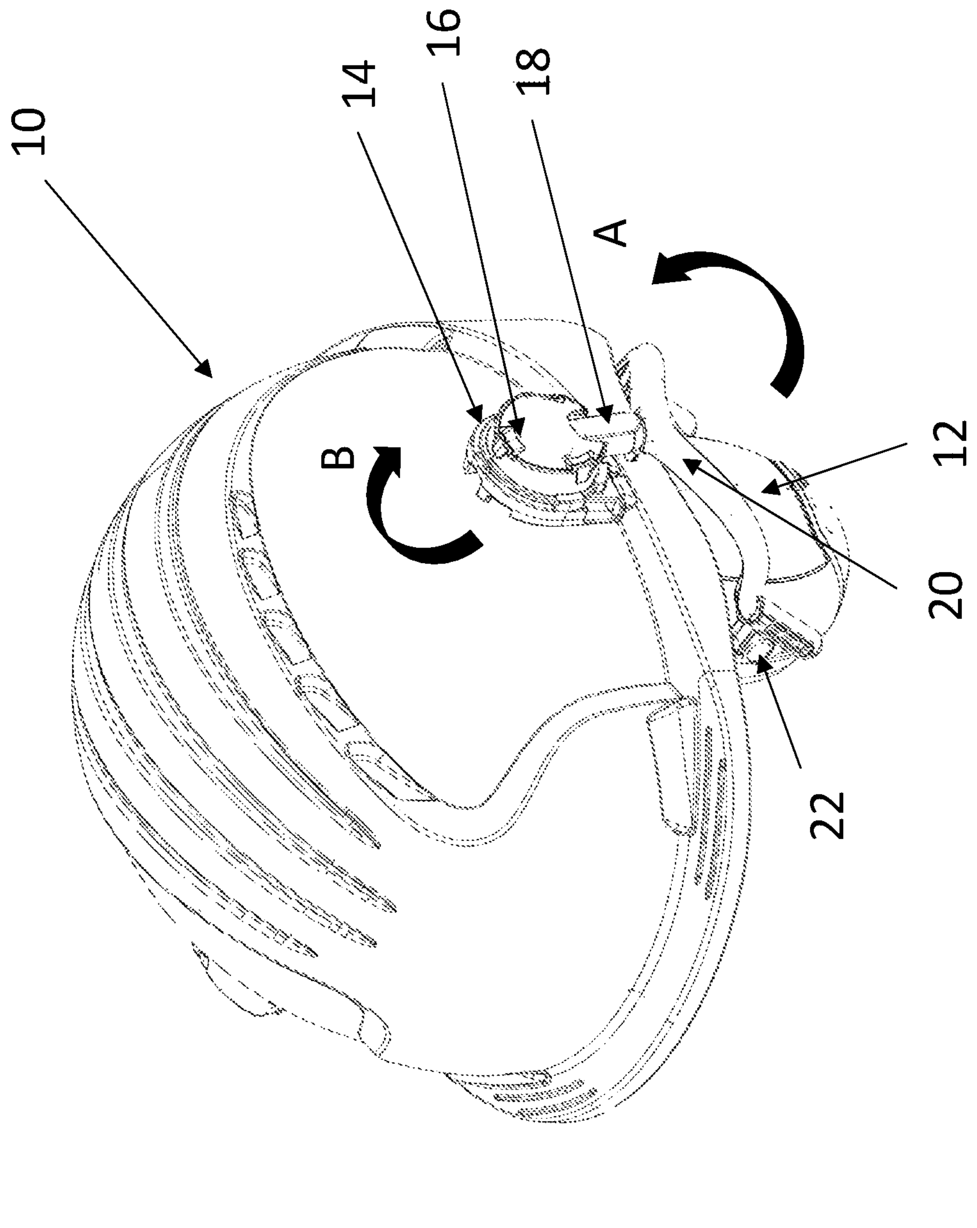
FIG. 1 shows a safety helmet according to an embodiment of the invention.

FIG. 1 shows an article of headwear comprising a safety helmet. The helmet comprises a protective head cover portion 10. A pair of earmuffs 12 (only one shown) are mounted, one on either side of the helmet at a peripheral region that is normally above a wearer's ears when in use. The earmuffs 12 are mounted on the helmet 10 by means of an adapter 14 carrying a housing 16. A socket 18 is mounted in the housing 16 such that one end projects from the housing. A mounting frame 20 is mounted in the socket 18 and the earmuffs 12 are connected to the mounting frame 20 by means of projections 22 extending from opposite sides of the earmuff 12.

Figure 2:
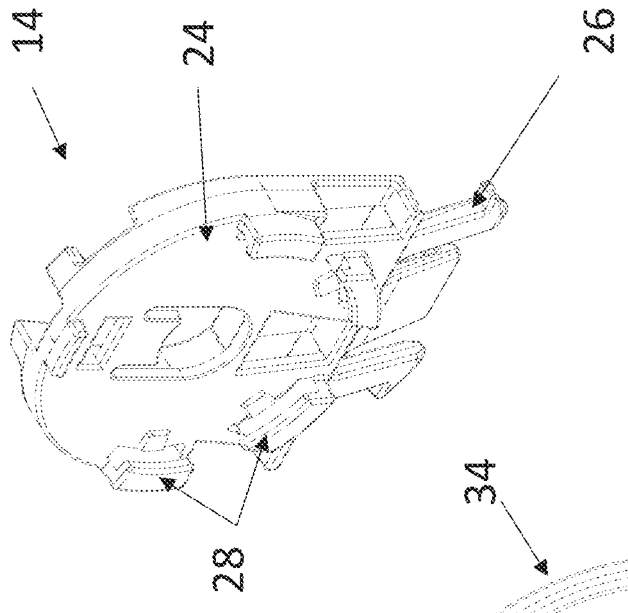
FIG. 2 shows further detail of the adapter shown in FIG. 1.

The adapter 14 is shown in more detail in FIG. 2. The adapter 14 comprises a generally circular base section 24 and a tongue section 26. The base section 16 is configured to locate the housing 16 as is described below. The tongue section 26 is configured to fit into a slot provided on the helmet 10 and latch against the sides of the slot to hold the adapter14 securely to the helmet 10 yet allow the adapter 14 to be removed when required. A series of locating tabs 28 are positioned around the periphery of the base section 24.

Figure 3:
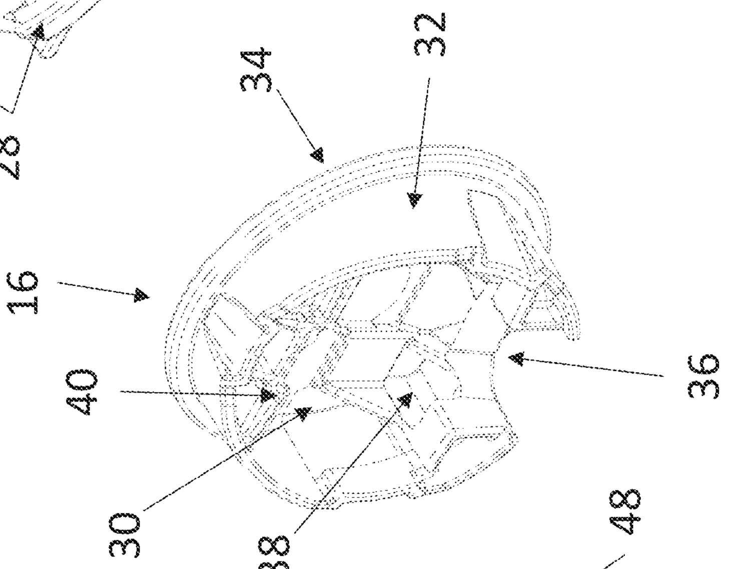
FIG. 3 shows further detail of the housing shown in FIG. 1.

The housing 16 is mounted on the adapter 14. FIG. 3 shows further detail of the housing, which comprises a generally circular base 30 having a sidewall 32 enclosing a space, and a radial flange 34 projecting from the base 30. The base 30 sits concentrically on the base section 24 of the adapter 14 such that the flange 34 fits behind the locating tabs 28. The housing 16 is free to rotate relative to the adapter 14. The sidewall 32 has a cut-out 36 and set formations 38 either side of the cut-out for mounting the socket 18. Spring supports 40 are provided within the space for locating a loop spring (not shown) for acting on the socket 18.

Figure 4:
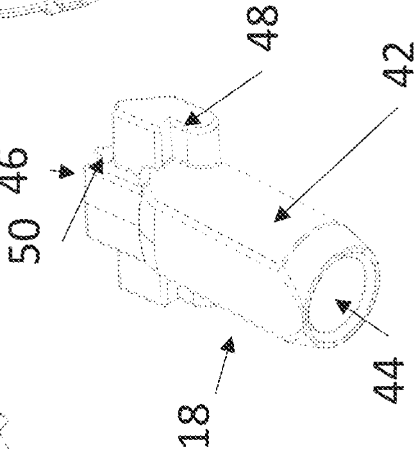
FIG. 4 shows further detail of the socket shown in FIG. 1.

The socket 18 is shown in more detail in FIG. 4 and comprises a tubular body 42 having an outer open end 44. The opposite inner end 46 has profiled projections 48 extending from opposite sides and a groove 50 across the end. The projections 48 sit in the seat formations 38 in the housing 16 so that the tubular body 42 projects through the cut-out 36. The loop spring sits between the spring supports 40 and groove 50 to hold the projections 48 into the seat formations 38.

Figure 5:
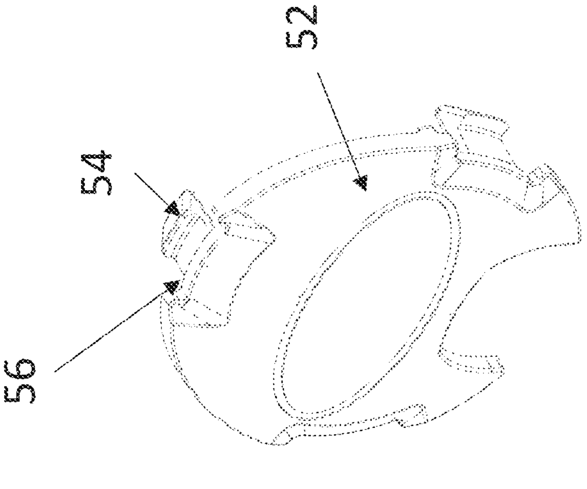
FIG. 5 show a cover used with the housing of FIG. 3.

A cover 52, as shown in FIG. 5, is fitted over the housing 16 to enclose the space inside the sidewall 32. The cover 52 is held onto the sidewall by flexible tabs 54 which engage in slots 56 in the sidewall 32.

Figure 6:
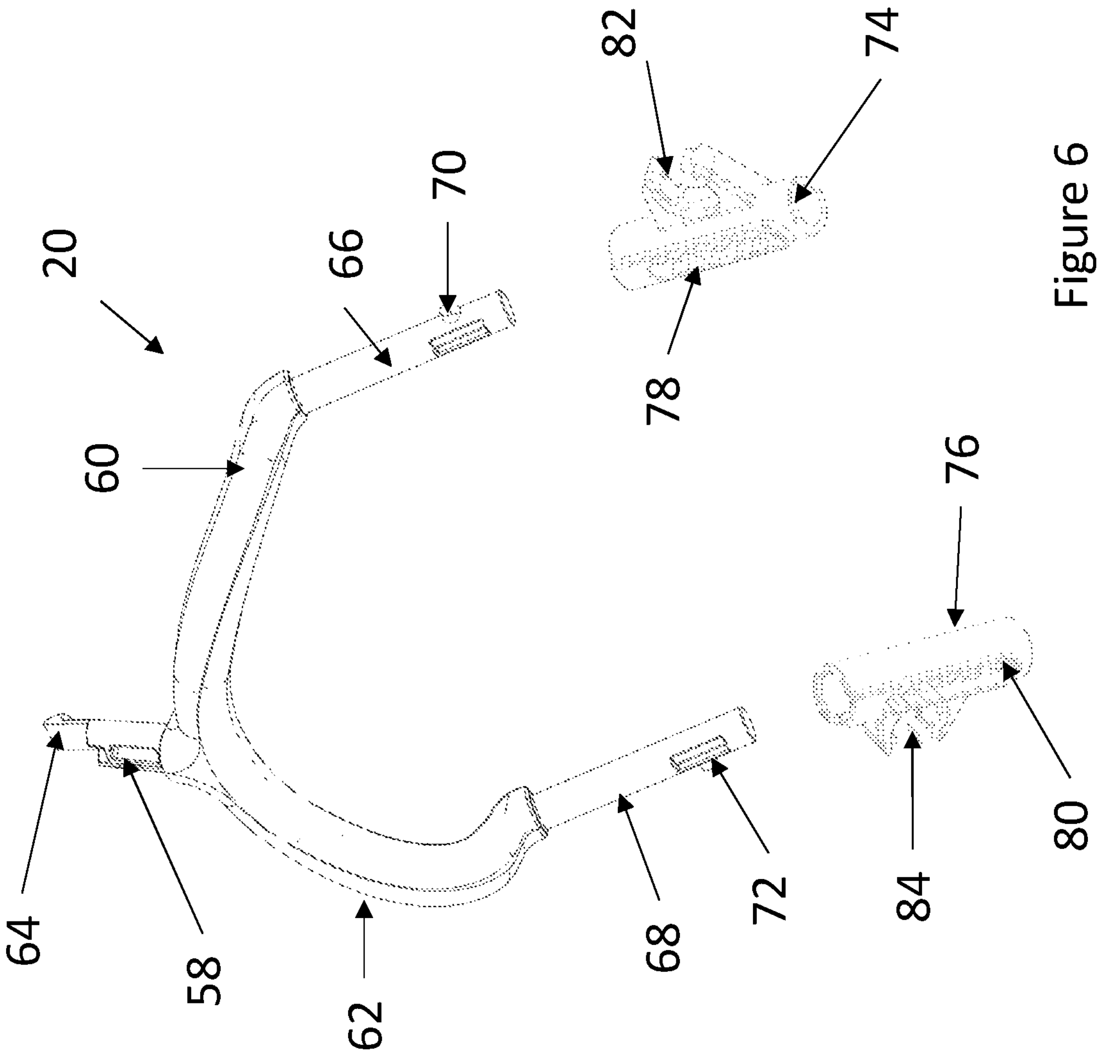
FIG. 6 shows further detail of the mounting frame 20 of FIG. 1.

FIG. 6 shows the mounting frame 20, which comprises a wishbone-shaped or Y-shaped structure having a shaft 58 with a pair of arms 60, 62 extending form one end of the shaft 58. The shaft 58 is shaped so as to fit inside the tubular body 42 of the socket 18. The other end of the shaft 58 has a latch 64 that engages a lip in the inner end 46 of the socket 18 when the shaft 58 is fully inserted into the tubular body 42. The prevents accidental disengagement of the mounting frame 20.

The arms 60, 62 are angled with respect to the shaft 58 so that when the socket 18 extends vertically down from the housing 16 (as shown in FIG. 1), the arms 60, 62 extend inwardly towards the wearer's head.

The ends 66, 68 of the arms 60, 62 are straight and parallel. Each end 66, 68 has a laterally projecting lug, or peg, 70, 72. A tubular extension 74, 76 having a notched or ridged slot 78, 80 fits over a respective end 66, 68 so that the lug 70, 72 sits in the slot 78, 80. A mounting bracket 82, 84 extends from the side of the lug 70, 72 so that the brackets 82, 84 both extend on the same side of the mounting frame 20 so that in use, the projections 22 on an ear muff 12 can be clipped into the brackets 82, 84 to secure the ear muff to the mounting frame 20 while allowing the earmuff 20 to pivot about an axis running between the projections 22.

The position of the extensions 74, 76 can be adjusted axially on the ends 66, 68 so that the lugs 70, 72 click from ridge to ridge or notch to notch. The ridges or notches serve to define predetermined positions for the extensions 74, 76. This is turn allows the position of the earmuff 12 to be adjusted relative to the helmet to properly fit a wearer.

In use, the action of the spring in the housing 16 urges the socket 18 towards the bottom of the cut-out 36 so that the tubular body 42 lies in plane parallel to that of the housing base 30. As is noted above, the angle of the arms 60, 62 means that the earmuff 12 is forced under the helmet 10 (this is the position shown in FIG. 1). A wearer's head will push the earmuffs out from this position but the earmuffs 12 will be held against the wearer's head by the action of the spring in the housing 16. The position of the extensions 74, 76 can be adjusted so that the earmuffs 12 sits comfortably over the wearer's ears.

If the wearer wishes to temporarily move an earmuff 12 away from their ear, they can push it outwardly from their head against the effect of the spring in the housing 16. The engagement of the projections 48 in the seat formations 38 means that the socket 18, mounting frame 20, and earmuff 12 will pivot around the projection 48 (arrow A in FIG. 1). The projections and seat formations 38 are shaped to define a stable limit position in which the socket 18 projects at an angle to the base 30 and is held in this limit position by the effect of the spring in the housing 16. To return the earmuff 12 to contact with the head, the wearer pulls the earmuff 12 down to move the projections 48 out of the stable limit position and the effect of the spring will push the earmuff 12 back against the wearer's head, as before.

If the wearer wishes to move the earmuffs 12 away for an extended period of time, they repeat the procedure described above to move the earmuff 12 away from their head. Once in this position, the housing 16 can be rotated on the adapter 14 to swing the socket 18, mounting frame 20 and earmuff 12 upwards (arrow B in FIG. 1) until the earmuff 12 is above the adapter 14. At this point, the earmuff 12 can be moved inwardly towards the helmet 10 and the effect of the spring in the housing 30 holds the earmuff against the helmet 10 until it is needed again. This procedure is reversed to bring the earmuff 12 back into use.

Figure 7:
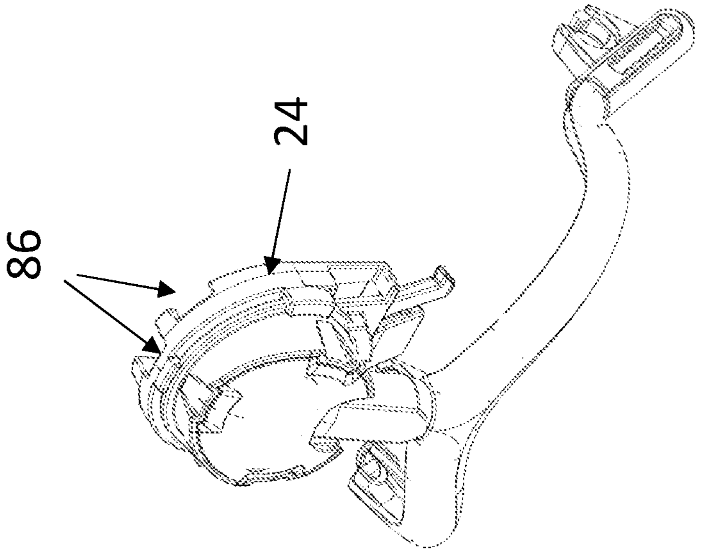
FIG. 7 shows the mounting device used in the helmet shown in FIG. 1.

FIG. 7 shows the mounting device comprising the adapter, housing, socket, and mounting frame in an in-use configuration as shown in FIG. 1 without the helmet 10 and earmuff 12. The upper part of the base section 24 has slots 86 for mounting accessories as is described below.

Figure 8:
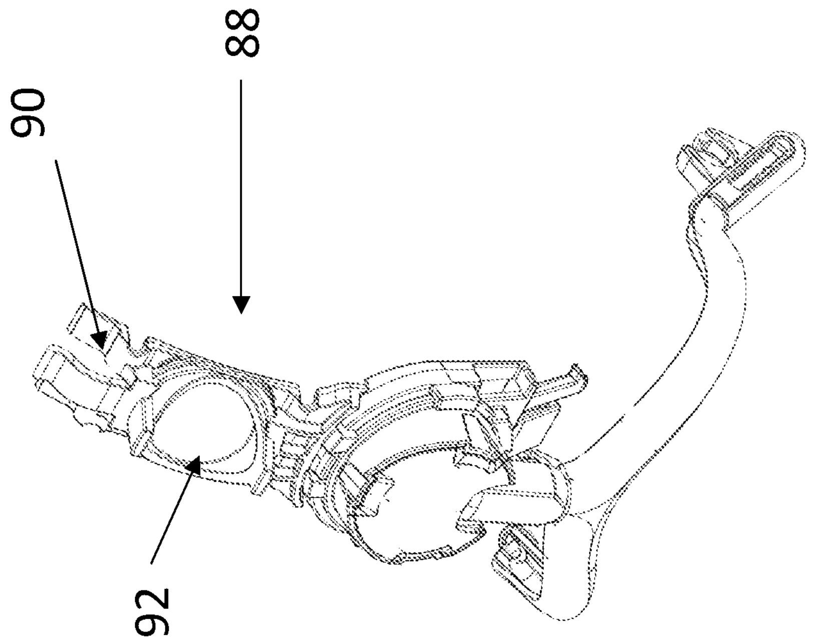
FIG. 8 shows a mounting device with an accessory holder.
Figure 9:
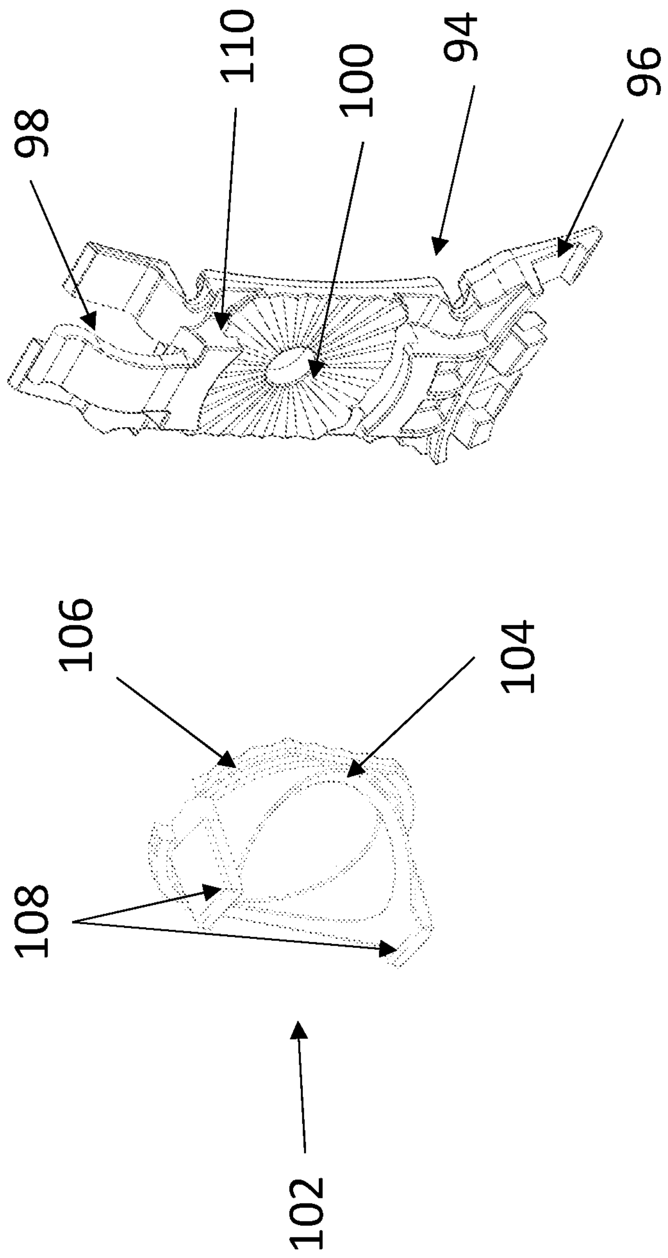
FIG. 9 shows the component parts of the accessory holder shown in FIG. 8.

FIG. 8 shows the mounting device of FIG. 7 with an accessory holder 88 fitted into the slots 86. The mounting device 88 has a clip section 90 for holding a writing implement such as a pen or pencil (not shown), and torch holder section 92. The accessory holder is formed from two parts as shown in FIG. 9. A frame part 94 has a tongue section 96 at one end that is configured to fit in the slots 86. The other end of the frame part 94 has spring clips 98 between which a pencil (not shown) can be held. The middle of the frame part 94 defines a torch holder mounting 100. A torch holder part 102 comprises a base 104 with a flange 106 and opposed arms 108 between which a torch can be fitted. In use, the torch holder part 102 is held on the frame part by engaging the flange 106 under lugs 110 on either side on the torch holder mounting 100. The torch holder part 102 can be rotated relative to the frame part to ensure that the torch points in the correct direction when installed on a helmet. Different accessory holder configurations can be used according to the type of accessory to be used.

Further changes can be made within the scope of the invention.

The invention claimed is:

1. A device for mounting an earmuff on an article of headwear, comprising:

a shell for positioning over a wearer's ear, with external mounting formations on opposite sides of the shell;

an adapter for connection to the article of headwear at a location on the periphery of the article of headwear that, is positioned above a wearer's ear;

a housing rotatably mounted on the adapter;

a socket having an inner end mounted in the housing and an open outer end projecting from the housing, wherein the socket is pivotable about an axis in the plane of rotation of the housing and is biased into either a first position in which the socket extends in a direction perpendicular to the axis of rotation of the housing or a second position in which the socket extends at an angle between the axis of rotation of the housing and the direction perpendicular to the axis of rotation; and a mounting frame comprising a shaft for engagement in the open end of the socket, and a pair of elongate arms extending from the shaft, wherein each arm has an extension with a mounting formation that is engageable with said external mounting formation on the shell, and wherein each extension is axially adjustable on its respective arm, such that when said earmuff is positioned between the arms, the mounting formations on opposite sides of the shell can engage in the mounting formations on respective extensions.

2. A device as claimed in claim 1, wherein the mounting formations on opposite sides of the shell are rotatable with respect to the mounting formations on the extensions.

3. A device as claimed in claim 1, wherein each extension and its respective arm have inter-engaging formations that are configured to limit axial adjustment to one of a predetermined number of axial positions.

4. A device as claimed in claim 3, wherein the inter-engaging formations comprise a peg in the arm which engages in a ridged slot in the extension, or vice versa.

5. A device as claimed in claim 1, wherein an end of the shaft comprises a latch which engages a lip in the socket to resist removal of the shaft from the socket.

6. A device as claimed in claim 1, wherein the socket comprises a pair of lateral extensions at its inner end that engage in a shaped seat in the housing to limit pivoting movement of the socket between the first and second positions.

7. A device as claimed in claim 6, further comprising a spring located within the housing that acts on the inner end of the socket to hold the lateral extensions in the shaped seat.

8. A device as claimed in claim 1, wherein the housing comprises a base and a cover, wherein the inner end of the socket is retained between the base and the cover.

9. A device as claimed in claim 1, wherein the adapter comprises a tongue portion that is configured to engage in a corresponding slot in the article of headwear.

10. A device as claimed in claim 1, wherein the adapter comprises a slot for mounting a holder for securing further items to the article of headwear.

11. An earmuff assembly for mounting on an article of headwear, comprising said device as claimed in claim 1 and said earmuff comprising the shell for positioning over a wearer's ear, with said external mounting formations on opposite sides of the shell, wherein the earmuff is positioned between the arms and the mounting formations on opposite sides of the shell are engaged in the mounting formations on said respective extensions.

12. An article of headwear, comprising a head cover portion adapted to be worn on a wearer's head, and an earmuff assembly as claimed in claim 11 connected to the article of headwear at a location on a periphery of the head cover portion that is positioned above a wearer's ear.

* * * * *